United States Patent [19]

Ito et al.

[11] Patent Number: 4,866,081
[45] Date of Patent: Sep. 12, 1989

[54] MICROBICIDAL PRESERVATIVE COMPOSITION

[75] Inventors: Yosuke Ito, Otsu; Yasuhiro Nomura, Takatsuki; Sakae Katayama, Higashiyodogawa, all of Japan

[73] Assignee: Buckman Laboratories International, Inc., Memphis, Tenn.

[21] Appl. No.: 103,820

[22] Filed: Oct. 2, 1987

[30] Foreign Application Priority Data

Oct. 17, 1986 [JP] Japan ................................ 61-248076

[51] Int. Cl.⁴ ............................................ A01N 31/00
[52] U.S. Cl. ................................... 514/367; 514/373; 435/243
[58] Field of Search ................. 435/243; 514/367, 373

[56] References Cited

FOREIGN PATENT DOCUMENTS 56-071009  6/1981  Japan ................................... 514/367

OTHER PUBLICATIONS

Dacre, J. C., "Preliminary Toxicological Evaluation of Eight Chemicals used as Wood Preservatives", Chem. Abstract No. CA102(13):107694f.

Primary Examiner—William R. Dixon, Jr.
Assistant Examiner—Anthony J. Green
Attorney, Agent, or Firm—Finnegan, Henderson, Farabow, Garrett & Dunner

[57] ABSTRACT

A composition comprising 2-(thiocyanomethylthio)-benzothiazole and 3-iodo-2-propinyl-N-butylcarbamate. The composition can be useful as a microbicidal preservative to prevent deterioration of raw materials such as dyes, pastes, lumber, leather, textiles and pulp caused by microorganisms.

23 Claims, 2 Drawing Sheets

MICROBICIDAL PRESERVATIVE COMPOSITION

FIELD OF THE INVENTION

The present invention relates generally to a composition and, more particularly, to a microbicidal preservative composition containing 2-(thiocyanomethylthio)-benzothiazole (hereafter "TCMTB") and 3-iodo-2-propinyl-N-butylcarbamate (hereafter "IPBC").

BACKGROUND OF THE INVENTION

Many chemicals such as organomercury compounds, organotin compounds, and chlorinated phenols have been used as industrial microbicidal preservatives. However, the toxicity of these compounds and environmental contamination caused by these compounds are known problems.

TCMTB and IPBC are known individually as low toxicity antimicrobials. When used alone, however, these compounds each possess a narrow antibacterial spectrum and have limited ability to completely prevent the growth of microorganisms.

SUMMARY OF THE INVENTION

The present invention can overcome the problems and disadvantages of the prior art by providing a composition comprising TCMTB and IPBC, preferably a low toxicity microbicidal preservative composition that can be effective against a wide range of microorganisms. The instant inventors discovered that the combined used of TCMTB and IPBC in a microbicidally effective amount can synergistically achieve superior microbicidal preservative activity at low concentrations against a wide range of microorganisms.

The present invention also provides a method for inhibiting the growth of a microorganism which comprises the step of contacting the microorganism with the composition of the invention in an amount synergistically effective to inhibit the growth of the microorganism. The invention also provides a method of preventing decay or deterioration of a material capable of supporting growth of a microorganism comprising the step of contacting the material with the composition of the invention in an amount synergistically effective to prevent the decay or deterioration of the material. The synergistically effective amount varies in accordance with the material or product to be treated and can readily be determined, without undue experimentation, by one skilled in the art.

The composition of the invention can be useful in preventing the deterioration of various types of industrial raw materials and products, such as dyes, pastes, lumber, leather, textiles and pulp, which are subject to decay and molding caused by microorganisms such as bacteria, mold and fungi.

Additional objects and advantages of the invention will be set forth in part in the description which follows, and in part will be obvious from the description, or may be learned by practice of the invention. The objects and advantages of the invention may be realized and obtained by means of instrumentalities and combinations particularly pointed out in the appended claims.

BRIEF DESCRIPTION OF THE DRAWINGS

The accompanying drawings, which are incorporated in and constitute a part of this specification, illustrate several embodiments of the invention and together with the description, serve to explain the principles of the invention.

Figure 1:
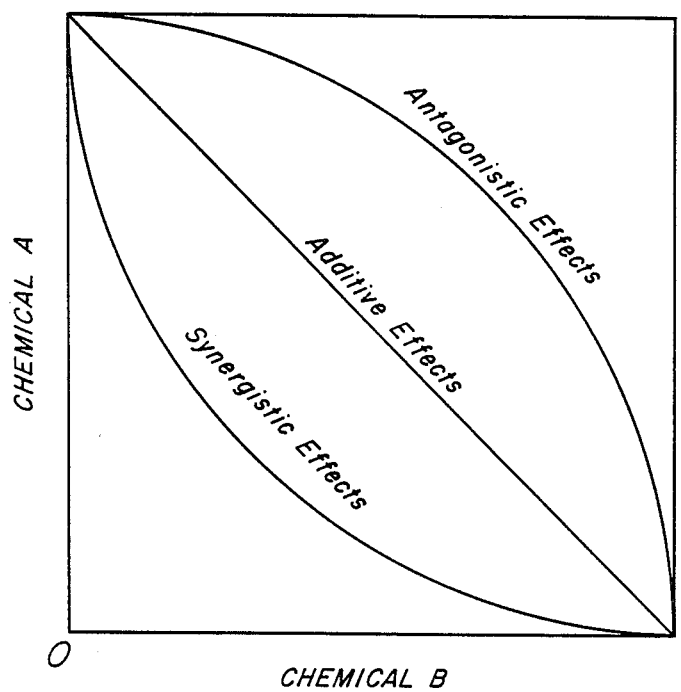
FIG. 1 is a graph showing the correlation between the chemical concentrations and interaction in minimal inhibitory concentration curves of a binary system.

The foregoing and other features and advantages of the present invention will be made more apparent from the following description of the preferred embodiments.

DETAILED DESCRIPTION OF THE PREFERRED EMBODIMENTS

Reference will now be made in detail to the preferred embodiments of the invention.

The present invention can provide a low toxicity microbicidal preservative composition comprising the combination of TCMTB and IPBC. The TCMTB and IPBC can be applied to a material or product capable of supporting the growth of a microorganism in an amount synergistically effective to inhibit the growth of the microorganism and thus prevent the decay or deterioration of the material or product.

The weight ratio of TCMTB:IPBC varies depending on the type of microorganism, material or product to which the composition is applied. One skilled in the art can readily determine, without undue experimentation, an appropriate weight ratio for a specific application. Preferably, the weight ratio of TCMTB:IPBC ranges from 1:30 to 30:1, more preferably, from 1:20 to 20:1, and most preferably, from 1:5 to 5:1.

The microbicidal preservative composition of the invention which combines the TCMTB and IPBC can demonstrate an unexpected synergistic effect compared to the respective components alone and thus achieves superior, i.e. greater than additive, microbicidal preservative activity at low concentrations against a wide range of microorganisms.

Depending upon the specific application, the composition of the invention may be prepared in various forms. The composition may be prepared in liquid form by dissolving the composition in an organic solvent. The liquid form is particularly useful to prevent the decay and molding of starch paste, wet pulp and wood. The preservative may be prepared in emulsion form by emulsifying it in water and, if necessary, adding a surfactant.

When the subject to be treated is a powder, the composition can be used in powder form; however, the TCMTB is preferably deposited on a carrier such as diatomaceous earth or kaolin and mixed with IPBC. The composition may be prepared in paste form by dissolving it in an organic solvent and adding a surfactant, and then applied to wood to prevent decay and molding. Additional chemicals such as insecticides may be added to the foregoing preparations.

The invention will be further clarified by the following examples, which are intended to be merely illustrative of the present invention.

EXAMPLE 1:

Preparation Examples

Four compositions were prepared using the components and weight percents set forth in Table 1.

TABLE 1

|  | Preparation 1 | Preparation 2 | Preparation 3 | Preparation 4 |
|---|---|---|---|---|
| TCMTB[1] | 13.3 | 10 | 6.7 | 25 |
| IPBC[1] | 6.7 | 10 | 13.3 | 25 |
| Eleminol[1,2] |  |  |  |  |
| ES-70 | 10 | 10 | 10 | 0 |
| Toxanone P8H[1,2] | 15 | 15 | 15 | 0 |
| Diethylene[1] |  |  |  |  |
| Glycol | 55 | 55 | 55 | 50 |

EXAMPLE 2

Synerguistic Effect of the Combined Use of TCMTB and IPBC Against Bacteria Subtilis

A. Binary Dilution Method

The synergistic effects between the TCMTB and IPBC were measured by the binary dilution method. TCMTB and IPBC were diluted to different concentrations and added to culture medium. Each preparation of TCMTB, IPBC and medium was then inoculated with microorganisms and cultured under set conditions. The fractional concentration of the undiluted solution at which no growth of microorganisms was found was taken as the minimal inhibitory concentration by the binary dilution method.

FIG. 1 is a graph of the minimal inhibitory concentration of each component on the axes using common scale coordinates. The region above the curve of the graph, i.e., the TDMIC curve, shows the proliferation inhibition region. The region below shows the proliferation region. Agreement of the diagonal and the TDMIC curve indicates additive effects. The extension of the curve above the diagonal shows antagonistic effects. The extension of the curve below the diagonal shows synergistic effects.

B. Synergistic Effect Against Bacillus Subtilis

The synergistic effect of the combined use of TCMTB and IPBC against Bacillus subtilis of the genus Bacillus which is a type of bacteria detected frequently in decayed matter such as latex, starch paste, starch slurry, and coating color was measured by the binary dilution method.

Bouillon medium was used as the medium, which was inoculated with a set quantity of a bacterial solution that had been precultured overnight. After shake culturing for 24 hours at 37° C., the concentration at which no turbidity of the medium was found was determined.

Figure 2:
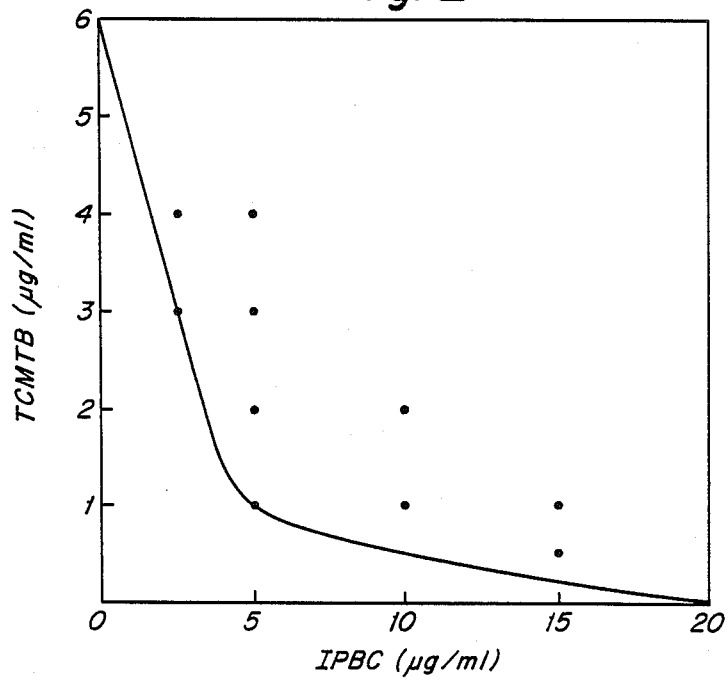
FIG. 2 sets forth a minimal inhibitory concentration curve of the microbicidal preservative composition of the invention against *Bacillus subtilis*.

The results are shown in FIG. 2. As shown in FIG. 2, the TDMIC curve against Bacillus subtilis demonstrated clear synergistic effects. Complete inhibition of bacterial growth appeared, for example, at a TCMTB concentration of 1 µg/ml and an IPBC concentration of 5 µg/ml. Since, as shown in FIG. 2, bacterial growth was inhibited individually by 6 µg/ml of TCMTB and 20 µg/ml of IPBC, the composition of the present invention demonstrated remarkable synergistic effects at approximately 1/5 of the sum of the necessary quantities of each component when used individually. Additional combinations of concentrations that demonstrate synergistic effects are set forth in Table 2:

TABLE 2

| TCMTB (µg/ml) | IPBC (µg/ml) |
|---|---|
| 0.5 | 15.0 |
| 0.5 | 10.0 |
| 1.0 | 15.0 |
| 1.0 | 10.0 |
| 2.0 | 10.0 |
| 2.0 | 5.0 |
| 3.0 | 5.0 |
| 3.0 | 2.5 |
| 4.0 | 5.0 |
| 4.0 | 2.5 |

EXAMPLE 3:

Synergistic Effect of the Combined Use of TCMTB and IPBC Against Aspergillus Niger The synergistic effect of the combined use of TCMTB and IPBC was evaluated against Aspergillus niger of the species Aspergillus which is a type of mold that develops frequently in wet pulp, starch paste and coating color.

Czapek medium was used as the medium. Spores from previous slant culture stock strains were collected. The medium was inoculated with a set quantity of liquid suspended in sterilized water. After shake culturing for 72 hours at 27° C., the concentration at which no mycelial growth was found in the medium was determined.

Figure 3:
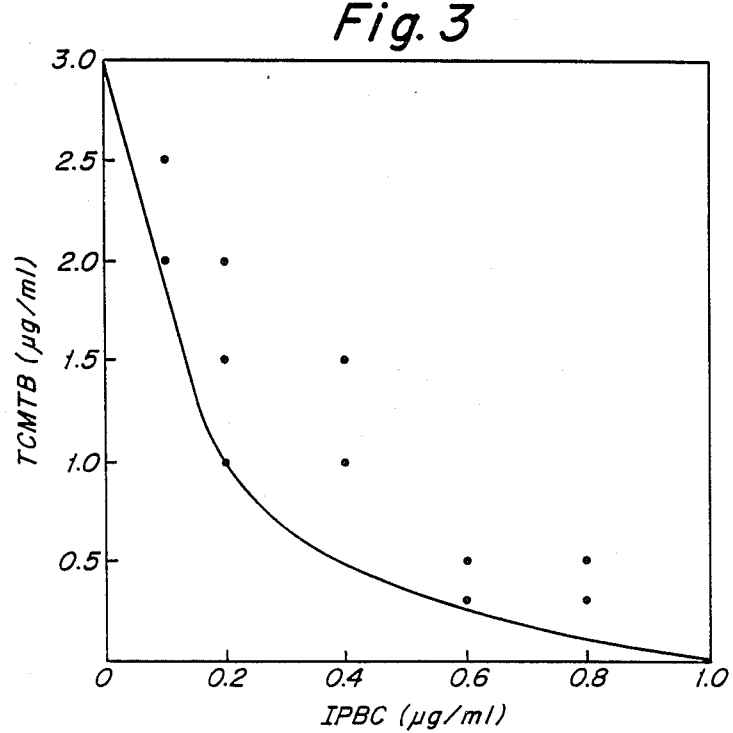
FIG. 3 sets forth a minimal inhibitory concentration curve of the microbicidal preservative composition of the invention against *Aspergillus niger*.

The results are shown in FIG. 3.

As shown in FIG. 3, the TDMIC curve against Aspergillus niger demonstrated clear synergistic effects. The concentration of TCMTB and IPBC at which complete inhibition of growth of the organisms appeared at a TCMTB concentration of 1.0 µg/ml and IPBC concentration of 0.2 µg/ml. Since growth of the organisms was inhibited individually by 3.0 µg/ml of TCMTB and 1.0 µg/ml of IPBC, the composition of the present invention demonstrated strong synergistic effects by permitting inhibition at approximately ¼ of the sum of the necessary quantities of each component when used individually. Additional combinations of concentrations of TCMTB and IPBC that demonstrated synergistic effects are set forth in Table 3.

TABLE 3

| TCMTB (µg/ml) | IPBC (µg/ml) |
|---|---|
| 0.3 | 0.8 |
| 0.3 | 0.6 |
| 0.5 | 0.8 |
| 0.5 | 0.6 |
| 0.5 | 0.4 |
| 1.0 | 0.4 |
| 1.5 | 0.4 |
| 1.5 | 0.2 |
| 2.0 | 0.2 |
| 2.0 | 0.1 |

EXAMPLE 4:

Preservative Effect of the Composition of the Invention In Starch Paste Solution Starch paste was prepared by dispersing cornstarch in a weight ratio of 5% in water and heating to 90° to 95° C. while stirring. After cooling, 1% already decayed paste solution was added and 100 g portions were poured into 140 ml glass bottles. Preparation 3 (set forth above in Table 1) was added to make the concentrations set forth in Table 4. Culture was conducted at 37° C., and bacterial counts were measured over a 10 day period. The results are shown in Table 4.

TABLE 4

| Days Elapsed | Added Concentration (mg/l) | | | |
|---|---|---|---|---|
| | 0 | 100 | 200 | 300 |
| 0 | 3.1 × 10$^5$ | | | |
| 2 | 6.3 × 20$^8$ | 8.0 × 10$^5$ | <10$^2$ | <10$^2$ |
| 4 | 3.6 × 10$^7$ | 9.4 × 10$^8$ | 6 × 10$^2$ | <10$^2$ |
| 6 | 7.6 × 10$^7$ | 2.5 × 10$^7$ | 4.1 × 10$^3$ | <10$^2$ |
| 8 | 8.9 × 10$^7$ | 4.1 × 10$^7$ | 1.8 × 10$^4$ | <10$^2$ |
| 10 | 9.7 × 10$^7$ | 6.8 × 10$^7$ | 5.8 × 10$^5$ | <10$^2$ |

As shown in Table 4, the addition of 300 mg/liter of Preparation 3 prevented decay of cornstarch paste.

EXAMPLE 5:

Microbicidal Activity of the Composition of the Invention in Wet Pulp

A slurry with a pulp concentration of 3% was prepared by macerating wet pulp (LBKP). 100 g portions were poured into polyethylene bottles and the chemicals of Preparation 4 (set forth above in Table 1) were added in the concentrations in relation to the pulp dry weight set forth in Table 5. After shaking with a shaker for 10 minutes, sheets were prepared by suction filtering the pulp by a Nutsche 5 cm in diameter. The sheets were punched to 4 cm in diameter and allowed to stand in petri dishes 9 cm in diameter which contained solidified medium which was prepared as follows.

To 1 liter of deionized water, 3.0 g of $NH_4NO_3$, 1.0 g of $KH_2PO_4$, 0.5 g of $MgSO_4.7H_2O$, 0.25 g of KCl, 0.002 g of $FeSO_4$ and 25 g of agar powder were added. Spores of the genera Asperqillus, Penicillium and Trichoderma which are frequently detected in wet pulp among molds isolated and stored from wet pulp, were suspended in sterilized water. Set quantities were then applied uniformly on top of the aforementioned sheets. Culture was conducted at 27° C. The growth conditions of the molds were examined individually over time and the effects evaluated. The results are shown in Table 5.

TABLE 5

| Days Elapsed | Added Concentration (mg/kg) | | | |
|---|---|---|---|---|
| | 0 | 25 | 50 | 100 |
| 2 | + | − | − | − |
| 5 | ++ | − | − | − |
| 10 | +++ | + | − | − |
| 15 | +++ | + | − | − |
| 20 | +++ | + | + | − |
| 25 | +++ | ++ | + | − |
| 30 | +++ | ++ | + | − |

The evaluation standards in Table 5 are as follows:
− :no mold development found on sheet
+ :mold development found on less than ⅓ of the sheet
++ :mold development found on ⅓ to ⅔ of the sheet
+++ :mold development found on ⅔ or more of the sheet As shown in Table 5, it was clear that mold development could be completely inhibited by adding 100 mg/kg of Preparation 4.

EXAMPLE 6:

Microbicidal Activity of the Composition of the Invention Against Fungi in Wood

A microbicidal test was conducted against molds that grow frequently in wood using Preparations 1, 2, and 3 (set forth above in Table 1).

The test method was in accordance with the wood fungicide fungicidal activity test method set forth in No. 2 of the Japan Wood Preservation Association (JWPA) standards described below. The test was conducted using the various amounts of chemical absorbed and the treatment concentrations set forth in Table 6. TCMTB and IPBC were prepared individually in the same manner as in Example 1 and are set forth in Table 6 for the sake of comparison. The microbicidal activity of the present invention was tested against the following fungi:

(1) *Aspergillus niger*
(2) *Penicillium funiculosum*
(3) *Aureobasidium pullulans*
(4) *Gliocladium riruns*
(5) *Rhizopus javanicus*

The test sheets were prepared as follows: Japanese beech sheets (20×3×50 mm) were immersed for 3 minutes in Preparations 1, 2, and 3 which were prepared to concentrations of 0.03%, 0.06% and 0.12% by weight, respectively, and the sheets were dried for 2 days.

Autoclave sterilized 2% agar solution was poured into sterilized petri dishes (90 mm in diameter) and solidified. A polypropylene mesh was placed on top as a frame to prevent direct contact between the test sheets and agar.

Three test sheets were placed on the stand and spore suspensions of the test molds were poured over the top. Six test sheets were used per concentration (2 sheets per dish). Culture was conducted for 4 weeks at 26° C. Evaluation was conducted by observing the growth conditions after 4 weeks. The evaluation values were determined according to the following standards.

| Evaluation Value | Growth Condition of Mold |
|---|---|
| 0 | Absolutely no mold growth found on test sheet |
| 1 | Mold development found only on sides of test sheet |
| 2 | Mold development found on less than ½ the surface area of the test sheet |
| 3 | Mold development found on more than ½ the surface area of the test sheet |

The damage values (D) in Table 6 were determined by the following equation by determining the total mean evaluation value (S) for each concentration of sample.

Total mean evaluation value $(S) = A_1 + A_2 + A_3 + A_4 + A_5$ ($A_1, A_2 \ldots A_5$: mean evaluation value of each mold species)

$$(D = (S_1 S_o) \times 100$$

$S_o$ Total mean evaluation value of untreated test sheets
$S_1$ Total mean evaluation value of treated test sheets of a certain concentration

TABLE 6

| Chemical | Chemical Treatment Concentration (%) | Amount of Chemical Absorbed (mg/m$^2$) | Mean Evaluation Value of Each Organism | | | | | S | D |
|---|---|---|---|---|---|---|---|---|---|
| | | | A$_1$* | A$_2$* | A$_3$* | A$_4$* | A$_5$* | | |
| TCMTB | 0.5 | 530 | 0 | 0 | 0 | 2.0 | 0 | 2.0 | 13 |
| alone | 0.3 | 300 | 0.5 | 0 | 0 | 2.3 | 0 | 2.8 | 19 |
| | 0.2 | 200 | 1.0 | 0.4 | 0 | 3 | 0 | 4.4 | 34 |
| IPBC | 0.12 | 110 | 0 | 0 | 0 | 0 | 1.3 | 1.3 | 9 |
| alone | 0.06 | 50 | 0 | 1.7 | 1.3 | 1.7 | 2.3 | 7 | 47 |
| | 0.03 | 26 | 0.7 | 2.0 | 2.0 | 26 | 3.0 | 10.3 | 69 |
| Preparation 1 | 0.12 | 100 | 0 | 0 | 0 | 0 | 1.7 | 1.7 | 11 |
| | 0.06 | 44 | 0 | 0 | 0 | 1.3 | 2.3 | 4.0 | 27 |
| | 0.03 | 23 | 0.3 | 0 | 0.7 | 1.7 | 1.7 | 4.4 | 29 |
| Preparation 2 | 0.12 | 110 | 0 | 0 | 0 | 0 | 0 | 0 | 0 |
| | 0.06 | 45 | 0 | 0 | 0 | 0 | 13 | 1.3 | 9 |
| | 0.03 | 22 | 0 | 0 | 0.3 | 1.0 | 1.7 | 3.0 | 20 |
| Preparation 3 | 0.12 | 103 | 0 | 0 | 0 | 0 | 1.3 | 1.3 | 9 |
| | 0.06 | 41 | 0 | 0 | 0 | 0.3 | 1.7 | 2.0 | 13 |
| | 0.03 | 25 | 0 | 0 | 0 | 1.7 | 2.0 | 3.7 | 25 |

*A$_1$: niger,
A$_2$: P. funiculosum,
A$_3$: A. pullulans,
A$_4$: G. virens,
A$_5$: R. gavaniaus As is evident from Table 6, microbicidal effects were demonstrated when the damage value (D) was no more than 30. A comparison with the individual test compounds showed that while the damage value of TCMTB alone of the comparative example was more than 30 at a concentration of 0.2% and that of IPBC alone was more than 30 at a concentration of 0.06% which indicate that essentially no microbicidal effects were obtained, the damage values of the compounds of the present invention were less than 30 even at the minimum test concentration of 0.03%.

It was, moreover, believed that TCMTB, which has inferior microbicidal effects to those of IPBC, would, in combination with IPBC, dilute the effects of IPBC alone from the standpoint of both concentration and efficacy. Nonetheless, the results in Table 6 show that the microbicidal activity of the combination of TCMTB and IPBC was vastly improved over that of IPBC alone. The superior effects are believed to be based on synergistic effects through combined use of the active ingredients. The most effective microbicidal activity resulted from the use of Preparation 2, wherein the mixture ratio of the TCMTB:IPBC was 1:1.

EXAMPLE 7:

Preservative Activity of the Composition of the Invention Aqainst Microorqanisms In Wood The preservative activity of the composition of the invention was determined against various types of organisms that decay wood.

The test compounds were prepared using the nonionic surfactant and glycol solvent with a mixture of TCMTB and IPBC in a weight ratio of 1:1 set forth above as Preparation 2. Solubilizing agents containing 20% by weight of TCMTB alone and 20% by weight IPBC alone were tested by the wood preservative activity test method set forth by No. 1 of the Japan Wood Preservation Association (JWPA) standards described below. The various concentrations shown in Table 7 were tested. TCMTB alone and IPBC alone, which were prepared in the same manner as previously set forth, are shown in Table 7 for comparison purposes.

The preservative activity of the composition was measured against the following organisms:

(1) Oouzuratake: *Tyromyces palustris*
(2) Kawaratake: *Coriolus versicolor*
(3) Namidatake: *Serpula lacrymans*

The test sheets were prepared as follows. The aforementioned aqueous emulsions prepared to concentrations of 0.5, 0.75, 1.5 and 2.0% by weight were applied uniformly by brush to make a proportion of 110 ±10 g/m$^2$ to sheets of Japanese cedar, red pine and Japanese beech (5×20×40 mm, flat surfaced, knot holes sealed by normal temperature curing epoxy type resin). After drying, the sheets were divided into two groups, one of which was submitted t a weathering test and one of which was not. After treating the former according to the JWPA weathering procedure, the two groups were dried to a constant weight at 60° C. and taken as the test sheets.

In the preservative activity test, JIS modified medium (peptone=0.5%, malt extract=1%, glucose=2.5%, KH$_2$PO$_4$=0.3%, MgSO$_4$.7H$_2$O=0.2%) was used as the medium and was inoculated with the organisms that decay wood. The test sheets of Japanese beech, Japanese cedar and Red pine and organisms that decay wood were combined as follows and cultured. *Tyromyces palustris* was applied to Japanese cedar; *Coriolus versicolor* was applied to Japanese beech and *Serpula lacrymans* was applied to red pine. Test culture of *Coriolus versicolor* and *Tyromyces palustris* was conducted for 56 days at 26 ±2° C. Test culture of *Serpula lacrymans* was conducted for 56 days at 20 ±2° C. The preservative activity values were determined. The results are shown in Table 7. The preservative activity values were calculated by the following formula.

Preservative activity value =

$$\frac{\text{Differences in mean weight loss percentage with and without chemical treatment}}{\text{Mean weight loss percentage of untreated sheets}} \times 100$$

An overall evaluation of the preservative activity of the present invention was possible by determining the high preservative activity values in combinations where a high weight loss was obtained in untreated sheets and comparing those values with the concentrations and amounts absorbed of wood preservatives that inhibited decay.

TABLE 7

| Test Compound | | Coriolus versicolor-Japanese beech | | Tryomyces palustris-Japanese cedar | | Serpula lacrymans-Red pine | |
| --- | --- | --- | --- | --- | --- | --- | --- |
| Name of Chemical | Concentration % | No Weathering Procedure | With Weathering Procedure | No Weathering Procedure | With Weathering Procedure | No Weathering Procedure | With Weathering Procedure |
| TCMTB Alone | 0.75 | 40 | 31 | 81 | 52 | 85 | 76 |
| | 1.00 | 54 | 33 | 87 | 55 | 93 | 90 |
| | 1.50 | 84 | 51 | 96 | 75 | 100 | 97 |
| | 2.00 | 97 | 86 | 100 | 100 | 100 | 100 |
| IPBC Alone | 0.50 | 82 | 71 | 75 | 70 | 89 | 82 |
| | 0.75 | 96 | 90 | 82 | 78 | 100 | 100 |
| | 1.00 | 100 | 98 | 96 | 93 | 100 | 100 |
| | 1.50 | 100 | 100 | 100 | 99 | 100 | 100 |
| Preparation 2 | 0.25 | 82 | 75 | 80 | 73 | 98 | 95 |
| | 0.50 | 100 | 91 | 100 | 89 | 100 | 100 |
| | 0.75 | 100 | 100 | 100 | 100 | 100 | 100 |
| | 1.70 | 100 | 100 | 100 | 100 | 100 | 100 |
| Untreated Weight Loss Percentage (%) | | 31.4 | | 33.2 | | 27.5 | |

"90" is the preservative activity value at which preservative effects are demonstrated. As is evident from Table 7, a comparison of Preparation 2 with each of the test compounds alone showed essentially no preservative effects (value less than 90) of the compounds alone at concentrations, for example, of 0.75% of TCMTB alone, and 0.5% of IPBC alone. For Preparation 2, however, the value was at least 90 for almost all concentrations. It was believed by those skilled in the art that the combination of TCMTB, which has inferior preservative effects, with IPBC would dilute the effects of IPBC when used alone. Nonetheless, the results in Table 7 show that the preservative activity values were greatly increased when TCMTB and IPBC were combined over those of IPBC alone. The superior results are believed to be based on synergistic effects through the combined use of these ingredients.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A microbiocidal composition consisting essentially of the combination of 2-(thiocyanomethylthio) benzothiazole and 3-iodo-2-propinyl-N-butylcarbamate in an amount synergistically effective to inhibit the growth of a microorganism.

2. The composition of claim 1 wherein the weight ratio of 2-(thiocyanomethylthio) benzothiazole:3-iodo-2-propinyl-N-butylcarbamate ranges from 1:30 to 30:1.

3. The composition of claim 1 wherein said weight ratio ranges from 1:20 to 20:1.

4. The composition of claim 3 wherein said weight ratio ranges from 1:5 to 5:1.

5. The composition of claim 4 wherein said weight ratio is

6. The composition of claim 1 further consisting essentially of an organic solvent.

7. The composition of claim 6 further consisting essentially of a surfactant.

8. The composition of claim 1 further consisting essentially of a surfactant.

9. The composition of claim 1 further consisting essentially of a carrier selected from the group consisting of diatomaceous earth and kaolin.

10. A method of inhibiting the growth of a microorganism comprising the step of contacting said microorganism with a composition consisting essentially of 2-(thiocyanomethylthio)benzothiazole and 3-iodo-2-propinyl-N-butylcarbamate in an amount synergistically effective to inhibit the growth of said microorganism.

11. The method of claim 10 wherein said microorganism is a bacteria.

12. The method of claim 11 wherein said bacteria is *Bacillus subtilis.*

13. The method of claim 10 wherein said microorganism is a mold.

14. The method of claim 13 wherein said mold is *Aspergillus niger.*

15. The method of claim 10 wherein said microorganism is a fungus.

16. The method of claim 10 wherein said microorganism is selected from the group consisting of Aspergillus, Penicillium and Trichoderma.

17. The method of claim 10 wherein said microorganism is selected from the group consisting of *Aspergillus niger, Penicillium funiculosum, Aureobasidium pullulans, Gliocladium riruns* and *Rhizopus javanicus.*

18. A method of preventing decay or deterioration of a material capable of supporting growth of a microorganism comprising the step of contacting said material with a composition consisting essentially of 2-(thiocyanomethylthio) benzothiazole and 3-iodo-2-propinyl-N-butylcarbamate in an amount synergistically effective to prevent the decay or deterioration of said material.

19. The method of claim 18 wherein said material is cornstarch paste.

20. The method of claim 18 wherein said material is wood.

21. The method of claim 18 wherein said material is wet pulp.

22. The method of claim 18 wherein said microorganism is selected from the group consisting of *Tyromyces palustris, Coriolus versicolor* and *Serpula lacrymans.*

23. The method of claim 18 wherein said microorganism is selected from the group consisting of *Aspergillus niger, Penicillium funiculosum, Aureobasidium pullulans, Gliocladium riruns,* and *Rhizopus javanicus.*

* * * * *

UNITED STATES PATENT AND TRADEMARK OFFICE
CERTIFICATE OF CORRECTION

PATENT NO. : 4,866,081

DATED : September 12, 1989

INVENTOR(S) : YOSUKE ITO et al.

It is certified that error appears in the above-identified patent and that said Letters Patent is hereby corrected as shown below:

Claim 5, column 9, line 62, after "is" insert --1:1.--; and

Claim 16, column 10, lines 41-42, "Aspergillus, Penicillium and Trichoderma" should be italicized.

Signed and Sealed this

Eleventh Day of September, 1990

Attest:

HARRY F. MANBECK, JR.

*Attesting Officer*     *Commissioner of Patents and Trademarks*